(12) United States Patent
Rodgers et al.

(10) Patent No.: US 9,649,625 B1
(45) Date of Patent: May 16, 2017

(54) CATALYSTS AND PROCESSES FOR PRODUCING ALDEHYDES

(71) Applicant: Eastman Chemical Company, Kingsport, TN (US)

(72) Inventors: Jody Lee Rodgers, Gilmer, TX (US); Joost Nicolaas Hendrik Reek, Amsterdam (NL); Xiaowu Wang, Amsterdam (NL)

(73) Assignee: Eastman Chemical Company, Kingsport, TN (US)

( * ) Notice: Subject to any disclaimer, the term of this patent is extended or adjusted under 35 U.S.C. 154(b) by 0 days.

(21) Appl. No.: 15/191,635

(22) Filed: Jun. 24, 2016

(51) Int. Cl.
  *C07C 45/50* (2006.01)
  *B01J 31/00* (2006.01)
  *B01J 31/24* (2006.01)

(52) U.S. Cl.
  CPC ........... *B01J 31/2404* (2013.01); *C07C 45/50* (2013.01); *B01J 2231/321* (2013.01); *B01J 2531/0205* (2013.01); *B01J 2531/26* (2013.01); *B01J 2531/822* (2013.01)

(58) Field of Classification Search
  CPC . C07C 45/50; B01J 31/2404; B01J 2231/321; B01J 2531/0205; B01J 2531/26; B01J 2531/822
  See application file for complete search history.

(56) References Cited

U.S. PATENT DOCUMENTS

| | | | |
|---|---|---|---|
| 5,817,884 A | 10/1998 | Bahrmann | |
| 8,692,027 B2 | 4/2014 | Norman et al. | |
| 8,710,275 B2 | 4/2014 | Norman et al. | |
| 8,921,608 B2 | 12/2014 | Norman et al. | |

FOREIGN PATENT DOCUMENTS

| | | |
|---|---|---|
| EP | 1 479 439 A1 | 11/2004 |
| EP | 1 888 680 A1 | 2/2008 |
| WO | WO 2008/094222 A2 | 8/2008 |

OTHER PUBLICATIONS

Adler, Alan D. et al.; "On the Preparation of Metalloporphyrins"; J. inorg. nucl. Chem., vol. 32; 1970; pp. 2443-2445.
Adler, Alan D.; "A Simplified Synthesis for meso-Tetraphenylporphin"; Journal of Organic Chemistry, vol. 32; 1967; p. 476.
Besset, Tatiana, et al.; "Supramolecular Encapsulated Rhodium Catalysts for Branched Selective Hydroformylation of Alkenes at High Temperature"; Advanced Synthesis and Catalysis; 2013; 6 pages.
Bowen, Richard J. et al.; "Convenient Synthetic Routes to Bidentate and Monodentate 2-, 3- and 4-pyridyl Phosphines: Potentially Useful Ligands for Water-Soluble Complex Catalysts"; Journal of Organometallic Chemistry, vol. 554; 1998; pp. 181-184.
Kamer, Paul C. J. et al.; "Chapter 3 Rhodium Phosphite Catalysts"; Rhodium Catalyzed Hydroformylation; 2000; pp. 35-62.
Kleij, Arjan W. et al.; "Encapsulated Transition Metal Catalysts Comprising Peripheral Zn(II)salen Building Blocks: Template-Controlled Reactivity and Selectivity in Hydroformylation Catalysis"; The Royal Society of Chemistry Communication; 2005; pp. 3661-3663.
Kleij, Arjan W. and Reek, Joost N. H.; "Ligand-Template Directed Assembly: An Efficient Approach for the Supramolecular Encapsulation of Transition-Metal Catalysts"; Chem. Eur. J., vol. 12; 2006; pp. 4218-4227.
Kleij, Arjan W. et al.; "Template-Assisted Ligand Encapsulation; the Impact of an Unusual Coordination Geometry on a Supramolecular Pyridylphosphine-Zn(II)porphyrin Assembly"; Inorganic Chemistry Communication, vol. 44, No. 22; 2005; pp. 7696-7698.
Kleij, Arjan W. et al.; "$Zn^{II}$-Salphen Complexes as Versatile Building Blocks for the Construction of Supramolecular Box Assemblies"; Chem. Eur. J, vol. 11; 2005; pp. 4743-4750.
Kluwer, Alexander, et al.; "Improved synthesis of monodentate and bidentate 2- and 3-pyridylphosphines"; Tetrahedron Letters, 48; 2007; pp. 2999-3001.
Kuil, Mark et al.; "High-Precision Catalysts: Regioselective Hydroformylation of Internal Alkenes by Encapsulated Rhodium Complexes"; Journal of American Chemical Society, vol. 128; 2006; pp. 11344-11345.
Meyer, W. H. et al.; "Tri (3-pyridyl) phosphine as amphiphilic ligand in rhodium-catalysed hydroformylation of 1-hexene"; Z. Naturforsch, vol. 62b; 2007; pp. 339-345.
Slagt, Vincent F. et al.; "Assembly of Encapsulated Transition Metal Catalysts"; Angew. Chem. Int. Ed., vol. 40, No. 22; 2001; pp. 4271-4274.
Slagt, Vincent F. et al.; "Encapsulation of Transition Metal Catalysts by Ligand-Template Directed Assembly"; Journal American Chemical Society, vol. 126; 2004; pp. 1526-1536.
Slagt, Vincent et al.; "Fine-Tuning Ligands for Catalysis Using Supramolecular Strategies"; European Journal of Inorganic Chemistry; 2007; pp. 4653-4662.
Van Leeuwen, Piet W. N. M.; "Chapter 1 Introduction to Hydroformylation, Phosphorus Ligands in Homogeneous Catalysis"; Rhodium Catalyzed Hydroformylation; 2000; pp. 1-8.
Van Leeuwen, Piet W. N. M. et al.; "Chapter 4 Phosphines as Ligands, Bite Angle Effects for Diphosphines"; Rhodium Catalyzed Hydroformylation; 2000; pp. 63-105.
Wajda-Hermanowicz, K. et al.; "Rhodium carbonyl complexes of the trans-[RhCl(CO)(PE3)2] type with psyridylphosphines"; Transition Met. Chem., vol. 13; 1988; pp. 101-103.
Yu, Yi et al.; "Ruthenium-Catalyzed Oxidation of the Porphyrin β,β'-Pyrrolic Ring: A General and Efficient Approach to Porpholactones"; Advanced Synthesis and Catalysis, 354; 2012; pp. 3509-3516.

*Primary Examiner* — Sikarl Witherspoon
(74) *Attorney, Agent, or Firm* — James Arnold, Jr.

(57) ABSTRACT

Use of a unique supramolecular assembly of a tris-pyridylphosphine ligand and a metal centered porphyrin complex modified with a lactone functional group was shown to have improved selectivities to branched aldehydes via rhodium catalyzed hydroformylation of unsubstituted linear alpha olefins such as propylene and 1-octene. The addition of potassium salts was also shown to increase the activity of the lactone modified porphyrin-based catalyst while maintaining similar branched aldehyde selectivities for propylene hydroformylation.

16 Claims, No Drawings

CATALYSTS AND PROCESSES FOR PRODUCING ALDEHYDES

BACKGROUND OF THE INVENTION

Iso-butyraldehyde derivatives are useful solvents and co-monomers in high performance polyesters; however, increasing demands for these materials have created unprecedented challenges for global iso-butyraldehyde production. Hydroformylation, the addition of hydrogen ($H_2$) and carbon monoxide (CO), mixtures of which are known as syngas, to an unsaturated bond is used to produce iso-butyraldehyde from propylene. This process provides a mixture of the linear product, normal-butyraldehyde (N), and the branched, iso-butyraldehyde product (I), with the ratio of normal- to iso- (N:I) typically being greater than or equal to two. The majority of hydroformylation research, particularly within industry, has focused on optimizing the normal aldehyde selectivity while interest in selectively forming the branched aldehyde has only recently emerged. Although an industrially viable process for iso-selective chemistry has yet to be developed, recent academic results have demonstrated highly branched hydroformylation of unsubstituted linear alpha olefins. Selectively hydroformylating at the C2 carbon position of these substrates is quite challenging given that unsubstituted linear alpha olefins bear no discerning electronic or steric features.

Avoiding costly separation of linear and branched aldehydes from the product stream is desirable to generate branched aldehydes in high concentration in an economical fashion. Thus, there remains a need to achieve reaction conditions conducive to achieving favorable N:I ratios from hydroformylation of unsubstituted linear alpha olefins while increasing reaction rates and efficiencies as demonstrated by higher turnover frequencies and/or turnover numbers.

SUMMARY OF INVENTION

According to an embodiment, the disclosure teaches a process for producing aldehydes, comprising contacting an olefin, with hydrogen and carbon monoxide in the presence of a catalyst composition to produce aldehydes, wherein the catalyst composition comprises a mixture of tris(3-pyridyl)phosphine, a zinc centered Meso-Tetraphenyl-2-oxa-3-oxoporphine coordination complex and a rhodium precursor.

In another embodiment, the disclosure teaches a process for producing aldehydes, comprising contacting an olefin, with hydrogen and carbon monoxide in the presence of a catalyst composition to produce aldehydes, wherein the catalyst composition comprises the following structure:

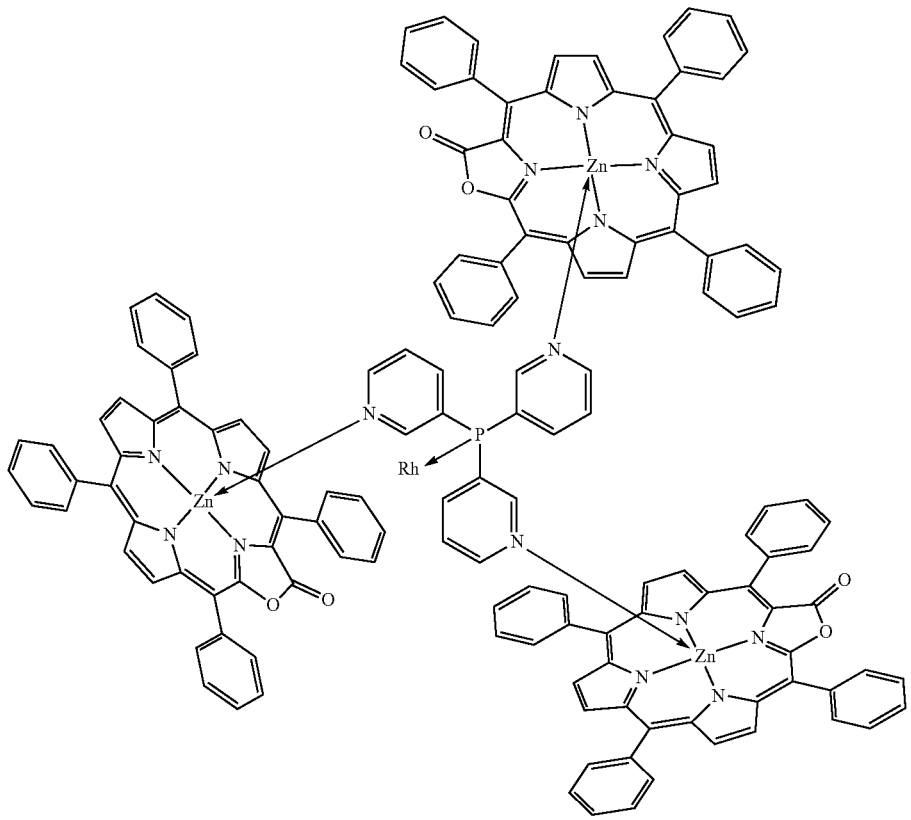

In another embodiment, the disclosure teaches a catalyst composition comprising a mixture of tris(3-pyridyl)phosphine, a zinc centered Meso-Tetraphenyl-2-oxa-3-oxoporphine coordination complex and a rhodium precursor.

In another embodiment, the disclosure teaches a method for preparing a catalyst composition comprising contacting a rhodium precursor with tris(3-pyridyl)phosphine, a zinc centered Meso-Tetraphenyl-2-oxa-3-oxoporphine coordination complex in a solvent to form the catalyst composition.

In another embodiment, the disclosure teaches a process for producing aldehydes, comprising contacting an olefin, with hydrogen and carbon monoxide in the presence of a catalyst composition to produce said aldehydes, wherein the catalyst composition comprises a mixture of tris(3-pyridyl)

phosphine, a zinc centered Meso-Tetraphenyl-2-oxa-3-oxoporphine coordination complex, a potassium precursor and a rhodium precursor.

In another embodiment, the disclosure teaches a catalyst composition comprising tris(3-pyridyl)phosphine, a zinc centered Meso-Tetraphenyl-2-oxa-3-oxoporphine coordination complex, a potassium precursor and a rhodium precursor.

In another embodiment, the disclosure teaches a method for preparing a catalyst composition comprising contacting a rhodium precursor and a potassium precursor with tris(3-pyridyl)phosphine, a zinc centered Meso-Tetraphenyl-2-oxa-3-oxoporphine coordination complex in a solvent to form the catalyst composition.

DETAILED DESCRIPTION

Possessing the ability to produce exclusively iso-butyraldehyde at commercially relevant rates would be a significant achievement for industrial hydroformylation processes. Selective synthesis of normal-aldehydes is relatively straightforward given the advances in ligand design over the past several decades. Efforts to produce the branched isomers from unsubstituted linear alpha olefins, however, have met with little success. In other words, methods for producing normal- to iso-aldehyde mixtures in a 1.2:1 to 25:1 ratio via rhodium catalysis are well established but industrial technologies for obtaining N:I ratios below 1.2:1 remain in their infancy. For purposes of this invention, N refers to normal (or linear) aldehydes which arise from hydroformylation of the C1 carbon of the olefin substrate and I refers to non-linear aldehydes which arise from hydroformylation of the C2 carbon of the olefin substrate. Moreover, for purposes of the invention, the terminology olefin, olefin substrate and substrate are used interchangeably.

According to an embodiment, the present disclosure demonstrates that modification of poryphyrin coordination complex such as, for example, the modification of Tetraphenylporphyrin coordination complex (5,10, 15, 20-Tetraphenyl-21H, 23H-porphine) described in U.S. Pat. No. 8,710,275, herein incorporated by reference, by adding a lactone to the complex can increase reaction rates and efficiencies within a hydroformylation reaction while maintaining acceptable N:I ratios.

The ligand system of the current disclosure is defined as a mixture of tris(3-pyridyl)phosphine (hereafter referred to as "PPy$_3$" or "phosphine ligand" or "ligand" or "phosphine" or "pyridylphosphine") and a lactone modified, zinc centered oxidized tetraphenylporphyrin coordination complex (hereafter referred to as "porphyrin complex" or "ZnTPPL" where zinc is the metal coordinated to the porphyrin) and a rhodium precursor. Moreover, the catalyst ligand system (or ligand system) according to the present invention is a composition comprising PPy$_3$ and a zinc centered tetraphenylporphyrin coordination complex and a rhodium precursor formed in situ under hydroformylation reaction conditions via insertion of an olefin into a rhodium carbonyl bond. Hence, according to an embodiment, a catalyst composition according to the present invention has the following structure:

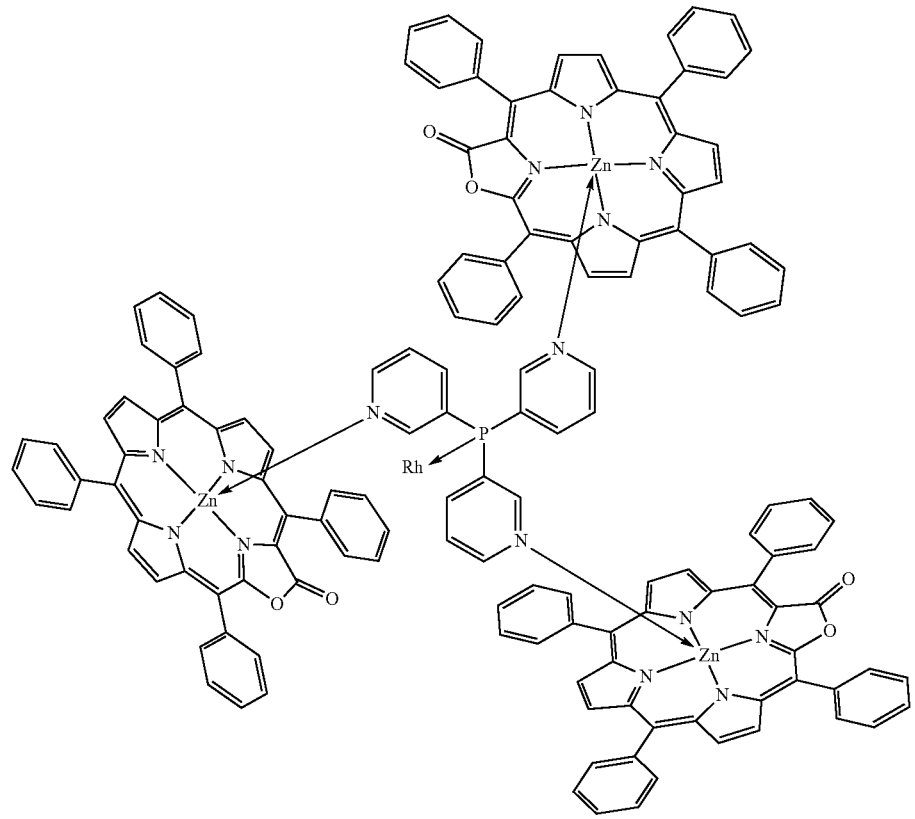

According to another embodiment, the rhodium precursor can be any rhodium containing complex or salt bearing spectator ligands such as, but not limited to, acetylacetonatobis(cyclooctene)rhodium(I); acetylacetonatobis(ethylene)

rhodium(I); acetylacetonatobis(1,5-cyclooctadiene)rhodium (I); bis(1,5-cyclooctadiene)rhodium(I) tetrafluoroborate; bis (1,5-cyclooctadiene)rhodium(I) trifluoromethanesulfonate; bis(norbornadiene)rhodium(I) tetrafluoroborate; chlorobis (cyclooctene)rhodium(I) dimer; chlorobis(ethylene)rhodium (I) dimer; chloro(1,5-cyclooctadiene)rhodium(I) dimer; chloronorbornadiene rhodium(I) dimer; rhodium(II) acetate dimer; rhodium(III) acetylacetonate; rhodium(III) bromide; rhodium(III) chloride; rhodium(III) iodide; rhodium(II) nitrate; rhodium (II) octanoate dimer; rhodium(II) trifluoroacetate dimer; tetrarhodium dodecacarbonyl; dirhodium tetraacetate dihydrate; rhodium(II) acetate; rhodium(II) isobutyrate; rhodium(II) 2-ethylhexanoate; rhodium(II) benzoate and rhodium(II) octanoate. Also, rhodium carbonyl species such as $Rh_4(CO)_{12}$; $Rh_6(CO)_{16}$; chlorodicarbonylrhodium (I) dimer and dicarbonylacetylacetonato rhodium(I) may be suitable rhodium feeds. Additionally, rhodium organophosphine complexes such as tris(triphenylphosphine)rhodium carbonyl hydride may be used when the phosphine moieties of the complex fed are easily displaced by the tris(3-pyridyl) phosphine ligand of the present invention.

According to another embodiment, the catalyst can be prepared by combining a rhodium precursor with tris(3-pyridyl)phosphine and the zinc centered tetraphenylporphyrin complex and an optional potassium precursor in a solvent. Examples of solvents include, but are not limited to, alkanes, cycloalkanes, alkenes, cycloalkenes, carbocyclic aromatic compounds, alcohols, esters, ketones, acetals, ethers and water. Specific examples of such solvents include alkanes and cycloalkanes such as dodecane, decalin, octane, iso-octane mixtures, cyclohexane, cyclooctane, cyclododecane, methylcyclohexane; aromatic hydrocarbons such as benzene, toluene, xylene isomers, tetralin, cumene; alkyl-substituted aromatic compounds such as the isomers of diisopropylbenzene, triisopropylbenzene and tert-butylbenzene; crude hydrocarbon mixtures such as naphtha, mineral oils and kerosene; high-boiling esters such as 2,2,4-trimethyl-1,3-pentanediol diisobutyrate. The aldehyde product of the hydroformylation process also may be used. The main criteria for the solvent is that it dissolves the catalyst and does not act as a poison to the catalyst. Examples of solvents for the production of volatile aldehydes, e.g., the butyraldehydes, are those that are sufficiently high boiling to remain, for the most part, in a gas sparged reactor. Solvents and solvent combinations that are preferred for use in the production of less volatile and non-volatile aldehyde products include 1-methyl-2-pyrrolidinone, dimethylformamide, perfluorinated solvents such as perfluorokerosene, sulfolane, water, and high boiling hydrocarbon liquids as well as combinations of these solvents. The optional potassium precursor can be any potassium containing salt such as, but not limited to, potassium acetate, potassium acetylacetonate, potassium benzyltrifluoroborate, potassium 2-ethyl hexanoate, potassium hexafluorophosphate, potassium methanesulfonate, potassium tetrafluoroborate, potassium tetraphenylborate, potassium tetra-p-chlorophenylborate, potassium tetraperfluorophenylborate, potassium toluenesulfonate Without being bound by any particular theory, it is believed that the additional of a potassium precursor to a ZnTPPL system increases TOF and/or TON because the potassium salt alters the ligand electronically in a way that is more conducive to iso-butyraldehyde formulation.

According to an embodiment, the mole ratio of metal porphyrin to tris(3-pyridyl)phosphine can be from about 1000:1 to 3:1 or from about 500:1 to about 100:1 or even from about 10:1 to 3:1. The mole ratio of tris(3-pyridyl) phosphine ligand to rhodium can be from about 1000:1 to about 1:1 or from about 500:1 to about 100:1 or even from about 100:1 to about 1:1. The mole ratio of potassium to rhodium can be from 1000:1 to about 1:1 or from about 500:1 to about 100:1 or even from about 100:1 to about 1:1. The mole ratio of substrate to rhodium can be from about 100000:1 to about 10:1 or from about 10000:1 to about 100:1 or even from about 5000:1 to about 1000:1. The pressure of the reaction can be from about 5000 psig to about 1 psig or from about 1000 psig to about 100 psig or even from about 500 psig to 200 psig. The temperature of the reactor can be from about 500° C. to about 0° C. or from about 100° C. to about 50° C. or even from about 90° C. to about 70° C. The ratio of carbon monoxide to hydrogen can be from about 100:1 to about 0.1:1 or from about 50:1 to about 10:1 or even from about 2.1:1 to about 1.9:1. The rate of reaction, or turnover frequency, can be from about 1000000 $h^{-1}$ to about 100 $h^{-1}$ or from about 100000 $h^{-1}$ to about 1000 $h^{-1}$ or even from about 10000 $h^{-1}$ to about 3000 $h^{-1}$. The N:I ratio of normal-aldehyde product relative to iso-aldehyde product can be from about 2:1 to about 0.01:1 or from about 1.5:1 to about 0.1:1 or even from about 1:1 to about 0.25:1.

According to an embodiment, the substrates used in these hydroformylation reactions are limited to unsubstituted linear alpha-olefins which are non-cyclic hydrocarbon molecules bearing a single carbon-carbon double bond between the first and second carbon atoms. The general formula of unsubstituted linear olefins in $C_nH_{2n}$ (where n is the number of carbon atoms) meaning that, due to unsaturation imposed by the double bond, the molecule has two less hydrogen atoms than the parent saturated hydrocarbon molecule. Examples of unsubstituted linear alpha-olefins include but are not limited to propylene, 1-butene, 1-pentene, 1-hexene, 1-heptene, 1-octene, 1-nonene, 1-decene, 1-undecene, 1-dodecene.

Examples of suitable reactor types include, but are not limited to, stirred tank, continuous stirred tank, and tubular reactors. Any of the known hydroformylation reactor designs or configurations may be used for the hydroformylation reaction to produce the aldehyde hydroformylation product. For example, the process may be conducted in a batchwise manner in an autoclave by contacting the substrate olefin with syngas in the presence of the catalyst compositions described herein. It will be apparent to those skilled in the art that other reactor schemes may be used with this invention. For example, the hydroformylation reaction can be conducted in a plurality of reaction zones, in series, in parallel, or it may be conducted batchwise or continuously in a tubular plug flow reaction zone or series of such zones with recycle of unconsumed feed substrate materials if required. The reaction steps may be carried out by the incremental addition of one of the feed substrate materials to the other. Also, the reaction steps can be combined by the joint addition of the feed substrate materials.

EXAMPLES

This invention can be further illustrated by the following examples of preferred embodiments thereof, although it will be understood that these examples are included merely for purposes of illustration and are not intended to limit the scope of the invention unless otherwise specifically indicated.

Abbreviations

TON=Turnover number; TOF=Turnover frequency; N=normal-aldehyde; I=iso-aldehyde; acac=acetylacetonate;

TPP=Tetraphenylporphyrin (5,10,15,20-Tetraphenyl-21H, 23H-porphine); TPPL=Meso-Tetraphenyl-2-oxa-3-oxoporphine; GC=Gas chromatography; Isom.=percent olefin isomerization. % Iso-=selectivity to branched aldehyde General The rhodium precursor, Rh(acac)(CO)$_2$ was purchased from Sigma-Aldrich (288101-1G 98%) and recrystallized from CH2CL2, and 1-octene was also purchased from Sigma-Aldrich (04806-IL, 98%) and filtered through basic aluminum oxide before use. Propylene (propene), purchased from Praxair (propene 2.5, 3H, content 1,100 kg) was delivered quantitatively to the reactors by a Brooks Quantim mass flow controller. The were prepared as described below. All chemical manipulations, unless otherwise stated, were carried out under an inert atmosphere. The ligand components used in the examples described below were tris(3-pyridyl)phosphine, ZnTPP and ZnTPPL prepared via the procedures described below:

Preparation of Tris(3-pyridyl)phosphine 1,2-Dibromoethane (2.0 mL, 23 mmol) was added dropwise to Mg turnings (7.0 g, 288 mmol) in 200 mL anhydrous THF, followed by the addition of 3-bromopyridine (10 mL, 103 mmol) at such a rate to maintain a steady reflux. The resulting mixture was heated at reflux at 56° C. for 30 minutes after the addition of 3-bromopyridine was complete, followed by the addition of 100 mL THF. The reaction mixture was slowly added via cannula to a solution of PCl$_3$ (2.2 mL, 25 mmol) in 50 mL THF at −78° C. After the addition was complete, the reaction mixture was allowed to warm to room temperature and stir overnight. The reaction was quenched with 5 mL N$_2$ bubbled water and all volatiles were evaporated to yield a yellow sticky solid. Afterwards, 200 mL diethylamine was added to the residue and the suspension was stirred for 30 minutes under N$_2$. The yellow precipitate was filtered off quickly by Büchner funnel and washed with diethylamine (3×70 mL). All organic fractions were collected and the solvent was quickly evaporated by rotary evaporator to gave bright yellow oil. The product was purified by flash column chromatography (silica, eluents: chloroform/hexane=2/1, 1% triethylamine) under N2 atmosphere. Yield 1.6 g (light yellow oil, 24% yield, afterwards low melting crystalline compound). 1H NMR (300 MHz, CDCl3, 295 K): δ=8.64 (m, 1H), 8.54 (m, 1H), 7.58 (m, 1H), 7.32 (m, 1H).

Preparation of ZnTPP

A solution of benzaldehyde (5.2 mL, 50 mmol, 1 eq) in propionic acid (130 mL) was heated to reflux at 122° C. During the reflux, pyrrole (3.5 mL, 50 mmol, 1 eq) was added to the reflux solution in 10 min. The reaction mixture was heated up to 130° C. for another 0.5 h. Afterwards, 50 mL of methanol was added to the reaction mixture and kept in the cold room overnight. The precipitates were collected by filtration and washed thoroughly with MeOH (10×20 mL) to yield purple powder in 4.6% yield (1.43 g, 2.3 mmol) of TPP-2H. TPP-2H (10 g, 16.2 mmol, 1 eq) and Zn(OAc)$_2$ (8.93 g, 48.6 mmol, 3 eq.) were dissolved in 400 mL of CHCl$_3$/EtOH=3:1. The reaction mixture was refluxed at 70° C. for 6 h. The reaction mixture was allowed to cool down and filtered over thin layer of Celite. The filtrate was concentrated and washed with 1000 mL methanol, which gave fine bright purple powder in 58% yield (6.4 g, 9.4 mmol). MeOH solution was concentrated and purified by column chromatography (silica gel, dichloromethane) to afford another 0.45 g crystalline purple solid. $^1$H NMR (400 MHz, CDCl3, 296 K): δ=8.96 (s, 12H, pyrrole), 8.23 (dd, J=7.6, 1.6 Hz, 8H, Ph), 7.76 (m, 12H, Ph).

Preparation of ZnTPPL

Step 1: To a stirred mixture of porphyrin (1.5 g, 2.4 mmol, 1 eq), RuCl$_3$ (248.9 mg, 1.2 mmol, 0.5 eq) in 1,2-dichloroethane (DCE) (750 mL) and water (750 mL), respectively, a DCE solution (20 mL) of 2,2'-bipyridine (187.4 mg, 1.2 mmol, 0.5 eq) was added. The solution was heated to 100° C. A mixture of Oxone® (7.377 g, 12 mmol, 5 eq) and NaOH (480 mg, 12 mmol, 5 eq) was added in 5 portions over a period of 5 h. The reaction was quenched with a saturated aqueous solution of Na$_2$S$_2$O$_3$, then the organic layer was separated and the aqueous layer was extracted by dichloromethane twice. The combined organic layer was dried by Na$_2$SO$_4$, filtered, and concentrated under vacuum. The residue was purified through a column (silica gel, CH2Cl2: hexane=2:1) to give the product porpholactone as a purple solid (yield 45%, 683.3 mg, 1.08 mmol). $^1$H NMR (500 MHz, CDCl$_3$, 293 K): δ=8.80 (dd, J=5.0, 1.7 Hz, 1H), 8.76 (dd, J=5.0, 1.8 Hz, 1H), 8.70 (dd, J=4.9, 1.7 Hz, 1H), 8.60 (d, J=4.9 Hz, 1H), 8.58 (dd, J=4.6, 1.4 Hz, 1H), 8.53 (d, J=4.5 Hz, 1H), 8.13 (m, 4H), 8.10 (m, 2H), 7.98 (m, 2H), 7.73 (m, 12H), −1.66 (s, 1H, NH), −2.03 (s, 1H, NH). Step 2: 5,10,15,20-Tetraphenylporpholactone (290 mg, 0.458 mmol, 1 eq) and Zn(OAc)$_2$ were suspended in a 120 mL solvent (CHCl$_3$:EtOH=2:1). The reaction mixture was heated up to 70° C. for 2 h. Afterwards, the reaction mixture was cooled down and filtered through Celite. The filtrate was concentrated and purified by column chromatography (silica gel, CH$_2$Cl$_2$, R$_f$=0.44). The bright green band was collected and all the solvent was evaporated which afforded green purple solid in 80% yield (255 mg, 0.366 mmol). $^1$H NMR (500 MHz, CDCl$_3$, 298 K): δ=8.72 (bs, 6H), 8.13 (bs, 6H), 7.8 (bs, 14H).

Calculations

Percent conversion=[(amount of octene isomers+amount of products)/(amount of 1-octene fed+amount of octene isomers+amount of products)]×100%

Percent isomerization (Isom.)=[(amount of internal octenes+amount of 2-propylhexanal+amount of 2-ethylheptanal)/(amount of 2-methyl-octanal+amount of nonanal+amount of internal octenes+amount of 2-propylhexanal+amount of 2-ethylheptanal)]×100%

Percent iso-aldehyde (% Iso)=[(amount iso-aldehyde)/(amount iso-aldehyde+amount normal-aldehyde)]×100%

Percent normal-aldehyde=[(amount normal-aldehyde)/(amount normal-aldehyde+amount iso-aldehyde)]×100%

TON=[(moles of desired aldehyde produced)/(moles of Rh(acac)(CO)$_2$)]

TOF=[(moles of desired aldehyde produced)/(moles of Rh(acac)(CO)$_2$)]/hour

Examples 1 and 2

These examples demonstrate the effect of using ZnTPPL instead of ZnTPP with the tris(3-pyridyl)phosphine Rhodium System at 25° C. with 1-Octene as the Substrate in a hydroformylation reaction.

Example 1

The hydroformylation reaction in Example 1 was carried out by preparing the pre-catalyst in a flame-dried schlenk (15 mL) under $N_2$ using the following substances: ZnTPP (30 μmol), $P(m-Py)_3$ stock solution in toluene (26 mM, 10 μmol), anhydrous toluene (5 mL), $Rh(acac)(CO)_2$ stock solution in anhydrous toluene (5 mM, 2 μmol), diisopropylethylamine (0.01 mL), 1-octene (filtered on basic alumina, 1.6 mL, 10214 μmol). A mini-autoclave (15 mL) was evacuated and flushed with $N_2$ three times. The Schlenk solution (without addition of 1-octene) was injected to the mini-autoclave via 10 mL stainless steel needle (~25 cm) under argon. 0.5 mL toluene was added to the Schlenk and transferred to the mini-autoclave. The system was flushed with syngas (30 bar, $H_2/CO=1:1$) three times. Then the autoclave was pressurized to 20 bar ($H_2/CO=1:1$), immersed into a pre-heated oil bath at 25° C. and stirred at 900 rpm for 1 hour. Afterwards, the pressure inside the reactor was released and 1-octene (filtered on basic alumina, 1.6 mL, 10214 μmol) was added via 15 mL stainless steel needle. The autoclave was then flushed with syngas (30 bar, $H_2/CO=1:1$) three times. Then the autoclave was pressurized to 30 bar syngas ($H_2/CO=1:1$) and adjusted to 20 bar. After 18 h, the autoclave was cooled down in an ice bath and then opened after the pressure was released.

Example 2

The hydroformylation reaction in Example 2 was carried out as described in Example 1 except that ZnTPPL was used instead of ZnTPP.

The results are summarized in Table 1. In both cases, the N/I of the resulting product was less than or equal to 0.6, and the ZnTPPL metalloporphyrin was nearly twice as active as the ZnTPP analog.

TABLE 1

| Example | Porphyrin | Substrate | Temp (° C.) | TON | TOF | N/I | % Iso- | Isom. |
|---|---|---|---|---|---|---|---|---|
| Ex. 1 | ZnTPPL | 1-Octene | 25 | 576 | 32 | 0.56 | 64.1 | 0.4 |
| Ex. 2 | ZnTPPL | 1-Octene | 25 | 1080 | 60 | 0.60 | 62.5 | 0.7 |

Examples 3 and 4

These Examples demonstrate the effect of using ZnTPPL instead of ZnTPP with the tris(3-pyridyl)phosphine Rhodium System at 25° C. with Propylene as the substrate in a hydroformylation reaction.

Example 3

The hydroformylation reaction in Example 3 was carried out as described in Example 1 except for the method of addition of reactant gases to the autoclave. A mini-autoclave (15 mL) was evacuated and flushed with $N_2$ three times. The Schlenk solution was injected to the mini-autoclave via 10 mL stainless steel needle (~25 cm) under argon. 0.5 mL toluene was added to the Schlenk and transferred to the mini-autoclave. The system was flushed with propene (8 bar) three times. Then the autoclave was charged with 8 bar propene (the volume is recorded by the flow meter). Afterwards, the gas in the charging line was released and the charging line was charged with the syngas from the gas mixing unit (~400 mL) with the desired $H_2:CO$ ratio of 1:3. The volume was recorded by the flow meter.

Example 4

The hydroformylation reaction in Example 4 was carried out as described in Example 3 except that ZnTPPL was used instead of ZnTPP The results are summarized in Table 2. ZnTPPL demonstrates a higher activity as well as better selectivity to branched aldehydes.

TABLE 2

| Example | Porphyrin | Substrate | Temp (° C.) | TON | TOF | N/I | % Iso- | Isom. |
|---|---|---|---|---|---|---|---|---|
| Ex. 3 | ZnTPPL | Propene | 25 | 1080 | 60 | 0.94 | 51.5 | N/A |
| Ex. 4 | ZnTPPL | Propene | 25 | 1350 | 75 | 0.84 | 54.3 | N/A |

Examples 5 and 6

These examples demonstrate the Effect of ZnTPP vs. ZnTPPL with the tris(3-pyridyl)phosphine Rhodium System at 70° C. with Propylene as the Substrate in a hydroformylation reaction.

Example 5

The hydroformylation reaction in this examples was carried out as described in Examples 3 except that the autoclave bath temperature was 70° C.

Example 6

The hydroformylation reaction in Example 6 was carried out as described in Example 5 except that ZnTPPL was used instead of ZnTPP.

The results are summarized in table 3. These examples demonstrate that with propene the ZnTPPL system also maintains a higher activity relative to ZnTPP.

TABLE 3

| Example | Porphyrin | Substrate | Temp (° C.) | TON | TOF | N/I | % Iso- | Isom. |
|---|---|---|---|---|---|---|---|---|
| Ex. 5 | ZnTPPL | Propene | 70 | 12870 | 715 | 1.12 | 47.2 | N/A |
| Ex. 6 | ZnTPPL | Propene | 70 | 16542 | 919 | 1.11 | 47.4 | N/A |

Examples 7 and 8

These examples demonstrates the effect of K:Rh using ZnTPPL with the tris(3-pyridyl)phosphine Rhodium System 60° C. with Propylene as the Substrate in a hydroformylation reaction.

Example 7

The hydroformylation reaction in this example was carried out as described in Example 4 except that the autoclave bath temperature was 60° C.

Example 8

The hydroformylation reaction in this example was carried out as described in Example 7 except a potassium salt (from $K[B(p-ClC_6H_4)]_4$) was added to give a K:Rh of 5, which describes the molar ratio of potassium to rhodium.

The addition of potassium to ZnTPPL shows markedly increased activity.

TABLE 4

| Example | Porphyrin | K:Rh | Substrate | Temp (° C.) | TON | TOF | N/I | % Iso- | Isom. |
|---|---|---|---|---|---|---|---|---|---|
| Ex. 7 | ZnTPPL | 0 | Propylene | 60 | 5940 | 330 | 1.13 | 46.9 | N/A |
| Ex. 8 | ZnTPPL | 5 | Propylene | 60 | 9810 | 545 | 1.12 | 47.1 | N/A |

The disclosure has been described in detail with particular reference to desirable embodiments thereof, but it will be understood that variations and modifications can be effected within the spirit and scope of the disclosure.

We claim:

1. A process for producing aldehydes, comprising contacting an olefin, with hydrogen and carbon monoxide in the presence of a catalyst composition to produce said aldehydes, wherein the catalyst composition comprises:
   a mixture of tris(3-pyridyl)phosphine, a zinc centered Meso-Tetraphenyl-2-oxa-3-oxoporphine coordination complex and a rhodium precursor.

2. A process according to claim 1, wherein the aldehydes are produced in an N:I ratio of from about 2.5:1 to about 0.01:1.

3. A process according to claim 2, wherein the N:I ratio is from about 2.3:1 to about 0.6:1.

4. The process according to claim 1, wherein the olefin is an unsubstituted linear alpha-olefin.

5. The process according to claim 4, wherein the olefin is propylene, 1-butene, 1-pentene, 1-hexene, 1-heptene, 1-octene, 1-nonene, 1-decene, 1-undecene, 1-dodecene or mixtures thereof.

6. The process according to claim 1, wherein a mole ratio of zinc centered Meso-Tetraphenyl-2-oxa-3-oxoporphine coordination complex to tris(3-pyridyl)phosphine is from about 1,000:1 to about 3:1.

7. The process according to claim 1, wherein a mole ratio of tris(3-pyridyl)phosphine ligand to rhodium precursor is from about 1000:1 to about 1:1.

8. The process according to claim 1, wherein a mole ratio of olefin to rhodium precursor is from about 100,000:1 to about 10:1.

9. The process according to claim 1, wherein a ratio of carbon monoxide to hydrogen can be from about 100:1 to about 0.1:1.

10. A process for producing aldehydes, comprising contacting an olefin, with hydrogen and carbon monoxide in the presence of a catalyst composition to produce aldehydes, wherein the catalyst composition comprises the following structure:

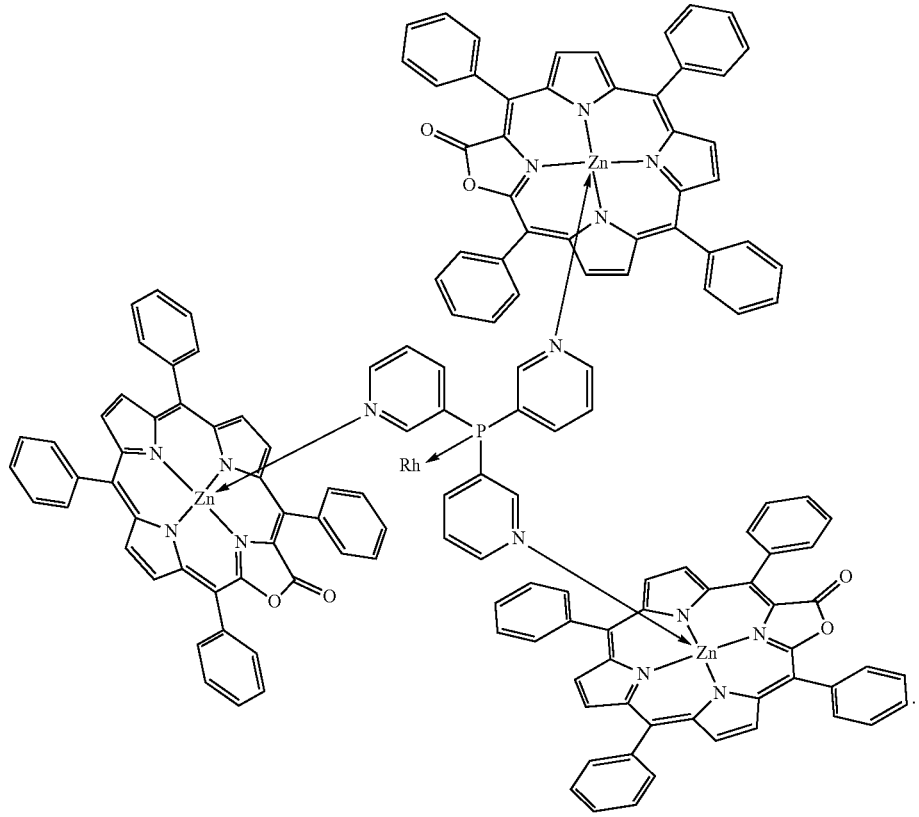

11. A catalyst composition comprising tris(3-pyridyl) phosphine, a zinc centered Meso-Tetraphenyl-2-oxa-3-oxoporphine coordination complex, and a rhodium precursor.

12. A method for preparing a catalyst composition comprising contacting a rhodium precursor with tris(3-pyridyl) phosphine, a zinc centered Meso-Tetraphenyl-2-oxa-3-oxoporphine coordination complex in a solvent to form the catalyst composition.

13. The method according to claim 12, wherein the solvent is a benzene, a toluene, a xylene, a pentane, a hexane, a heptane, an octane, a nonane, an ethyl acetate, a dichloromethane, a diethyl ether or mixtures thereof.

14. A process for producing aldehydes, comprising contacting an olefin, with hydrogen and carbon monoxide in the presence of a catalyst composition to produce said aldehydes, wherein the catalyst composition comprises:
   a mixture of tris(3-pyridyl)phosphine, a zinc centered Meso-Tetraphenyl-2-oxa-3-oxoporphine coordination complex, a potassium precursor and a rhodium precursor.

15. A catalyst composition comprising tris(3-pyridyl) phosphine, a zinc centered Meso-Tetraphenyl-2-oxa-3-oxoporphine coordination complex, a potassium precursor and a rhodium precursor.

16. A method for preparing a catalyst composition comprising contacting a rhodium precursor and a potassium precursor with tris(3-pyridyl)phosphine, a zinc centered Meso-Tetraphenyl-2-oxa-3-oxoporphine coordination complex in a solvent to form the catalyst composition.

* * * * *